United States Patent
Ishikawa et al.

(10) Patent No.: US 7,618,189 B2
(45) Date of Patent: Nov. 17, 2009

(54) BED APPARATUS, X-RAY DIAGNOSTIC APPARATUS, AND METHOD OF CONTROLLING A BED FOR X-RAY DIAGNOSTIC APPARATUS

(75) Inventors: Naobumi Ishikawa, Otawara (JP); Hayato Kasaoka, Otawara (JP); Norimitsu Kosugi, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 11/537,838

(22) Filed: Oct. 2, 2006

(65) Prior Publication Data

US 2007/0076852 A1  Apr. 5, 2007

(30) Foreign Application Priority Data

Oct. 3, 2005  (JP)  ............................ 2005-289977

(51) Int. Cl.
 *A61G 1/00* (2006.01)
(52) U.S. Cl. .......................................... 378/209; 5/601
(58) Field of Classification Search ......... 378/208–209; 5/601; 600/415
 See application file for complete search history.

(56) References Cited

U.S. PATENT DOCUMENTS

| 4,908,844 | A | * | 3/1990 | Hasegawa | .................... 378/209 |
| 5,345,632 | A | * | 9/1994 | Langenaeken et al. | .......... 5/601 |
| 6,353,949 | B1 | * | 3/2002 | Falbo | ............................. 5/610 |
| 6,773,161 | B2 | * | 8/2004 | Tanaka | ....................... 378/198 |
| 2005/0234327 | A1 | | 10/2005 | Saracen et al. | |

FOREIGN PATENT DOCUMENTS

| FR | 2 815 242 | 4/2002 |
| JP | 6-237926 | 8/1994 |
| JP | 7-299063 | 11/1995 |
| JP | 11-192222 | 7/1999 |
| JP | 11-285491 | 10/1999 |

* cited by examiner

*Primary Examiner*—Hoon Song
(74) *Attorney, Agent, or Firm*—Oblon, Spivak, McClelland, Maier & Neustadt, L.L.P.

(57) ABSTRACT

A bed apparatus includes a bed, a bed lifting unit that lifts the bed, and a bed stop position control unit that controls the bed lifting unit such that the bed stops at a position out of the maximum stroke according to a predetermined stop condition.

13 Claims, 7 Drawing Sheets

BED APPARATUS, X-RAY DIAGNOSTIC APPARATUS, AND METHOD OF CONTROLLING A BED FOR X-RAY DIAGNOSTIC APPARATUS

BACKGROUND OF THE INVENTION

1. Field of the Invention

The present invention relates to a bed apparatus for an X-ray diagnostic apparatus having a safety function for preventing a patient from falling, an X-ray apparatus and a method of controlling a bed for an X-ray diagnostic apparatus.

2. Description of the Related Art

As for diagnosis using an X-ray diagnostic apparatus, in some cases, an operator lifts a bed at about 90° from a horizontal position to lift a patient. In such diagnosis, in related art, when lifting a bed from a horizontal position to lifting position, an operator operates the bed such that a patient does not fall forward, constantly watching the condition of the patient.

A technology, which prevents displeasure and discomfort of a patient due to rapid change in speed of a bed and the patient from falling forward by changing a moving speed of a bed with respect to its lifting angle such that the speed is high at the first half and low at the later half, has been proposed (for example, JP-UM-A No. 2-63817).

However, in methods of lifting a bed, for patients bent or with weak legs, when the lifting angle of a bed reaches about 90°, the patients may fall forward or feel uneasy as if they fall forward. Accordingly, while constantly watching the condition of a patient, an operator should pay attention to the operation of a bed as stopping a lifting operation of a bed, when the patient seems to fall forward.

According to the above technology disclosed in JP-UM-A-2-63817, because only the speed of a bed changes, when a patient seems to fall forward, an operator needs to stop the lifting operation of a bed. Therefore, an operator should constantly watch the condition of a patient.

Such problems appear not only in a bed apparatus used in an X-ray diagnostic apparatus, but a bed for other medical instruments.

SUMMARY OF THE INVENTION

The invention has been finalized in order to solve the drawbacks inherent in the related art, and it is an object of the invention to provide a bed apparatus, an X-ray diagnostic apparatus, and a method of controlling a bed in an X-ray diagnostic apparatus that can reduce a burden of an operator and improve safety for a patient when an operator lifts the bed.

In order to achieve the above object, according to an aspect of the invention, a bed apparatus includes a bed, a bed lifting unit that lifts the bed, and a bed stop position control unit that controls the bed lifting unit such that the bed stops at a position out of the maximum stroke according to a predetermined stop condition.

In order to achieve the above objects, according to another aspect of the invention, an X-ray diagnostic apparatus includes a diagnostic information obtaining unit that obtains diagnostic information of an object by irradiating X-rays, a bed where the object placed, a bed lifting unit that lifts the bed, and a bed stop position control unit that controls the bed lifting unit such that the bed stops at a position out of a maximum stroke according to a predetermined stop condition.

In order to achieve the above objects, according to another aspect of the invention, a method of controlling a bed for an X-ray diagnostic apparatus includes lifting a bed and stopping the bed at a position out of a maximum stroke according to a predetermined stop condition.

A bed apparatus, an X-ray diagnostic apparatus, and a method of controlling a bed for an X-ray diagnostic apparatus according to the aspects of the invention can reduce a burden of an operator and improve safety for a patient when an operator lifts the bed.

DESCRIPTION OF THE PREFERRED EMBODIMENTS

Preferred embodiments of a bed apparatus, and X-ray diagnostic apparatus, and a method of controlling a bed for an X-ray diagnostic apparatus are described in detail hereafter with reference to accompanying drawings.

Figure 1:
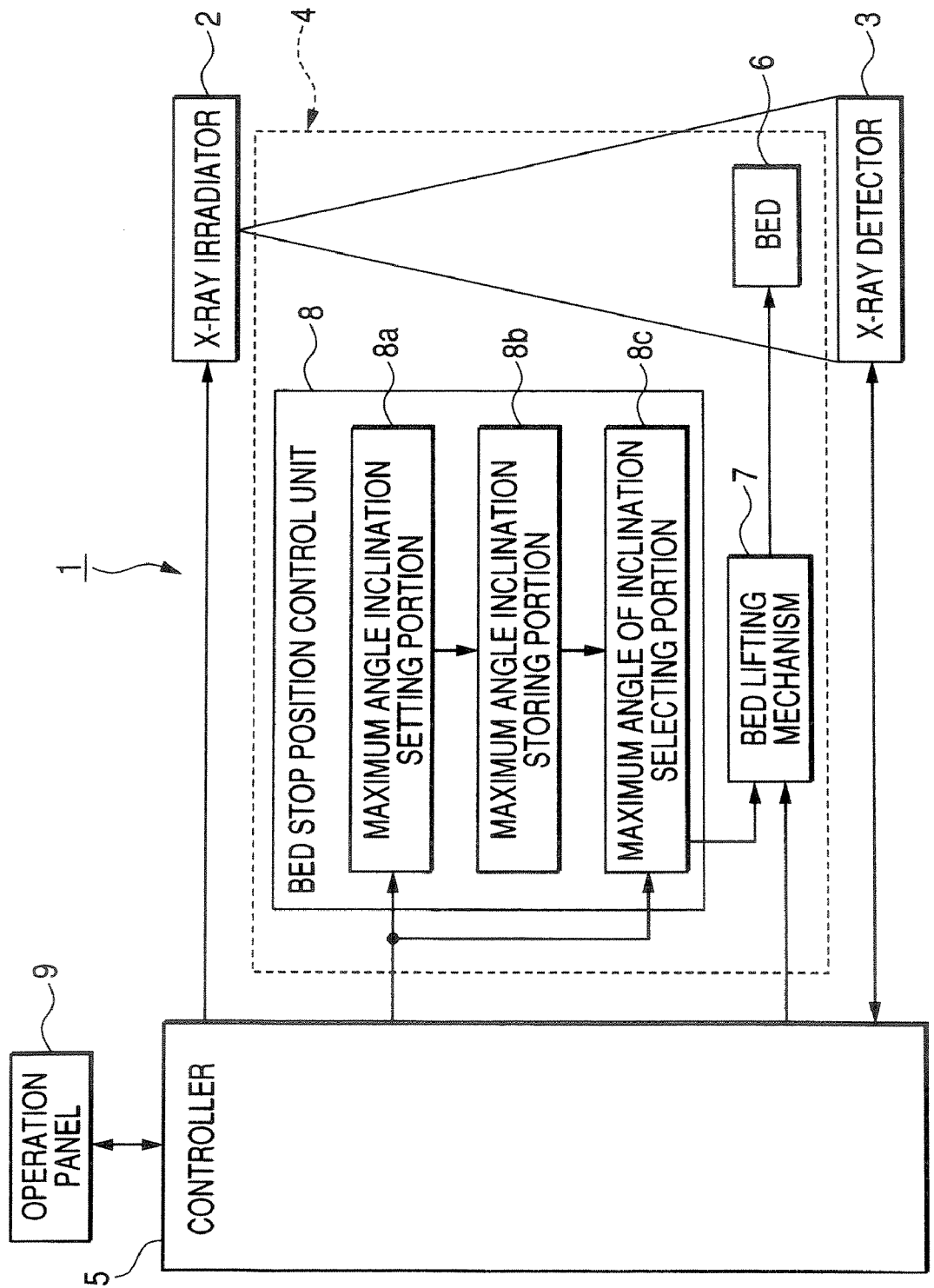
FIG. 1 is a block diagram illustrating a function of an X-ray diagnostic apparatus according to a first embodiment of the invention.

FIG. 1 is a block diagram illustrating a function of an X-ray diagnostic apparatus according to a first embodiment of the invention.

An X-ray diagnostic apparatus 1 includes an X-ray irradiator 2, an X-ray detector 3, a bed apparatus 4, and a controller 5. The bed apparatus 4 includes a bed 6, a bed lifting mechanism 7, and a bed stop position controller 8. The controller 5 is provided with an operation panel 9. The bed stop position controller 8 may be mounted in the controller 5. The controller 5 and the bed stop position controller 8 may be constructed by a circuit, but partially constructed by reading a program into an arithmetic unit of a computer.

The bed 6 is disposed between the X-ray irradiator 2 and the X-ray detector 3. An object, that is, a patient (not shown in FIG. 1) is placed on the bed 6. The X-ray irradiator 2 radiates X-rays to the object and the X-rays transmitting the object are detected by the X-ray detector 3. Detection signals detected by the detector 3 are transmitted to the controller 5 and used to create diagnostic information of the object such as an image.

The bed lifting mechanism 7 is controlled by a control signal out of the controller 5 and can lift the bed 6. The bed stop position controller 8 is also controlled by a control signal out of the controller 5 and can control the bed lifting mechanism 7 such that the bed 6 stops at a position out of a maximum stroke according to a predetermined stop condition.

The controller 5 has a function collectively controlling each component of the X-ray diagnostic apparatus 1. For example, the controller 5 has a function making the X-ray irradiator 2 irradiate X-rays by applying a high voltage to the X-ray irradiator 2 according to operating information inputted through the operation panel 9. Further, the controller 5 has a function controlling the bed lifting mechanism 7 and the bed stop position controller 8 by transmitting a control signal to them, and positions of the X-ray irradiator 2 and the X-ray detector 3, and other functions. In addition, the controller 5 obtains a detection signal detected by the X-ray detector 3 and creates an image of an object.

Figure 2:
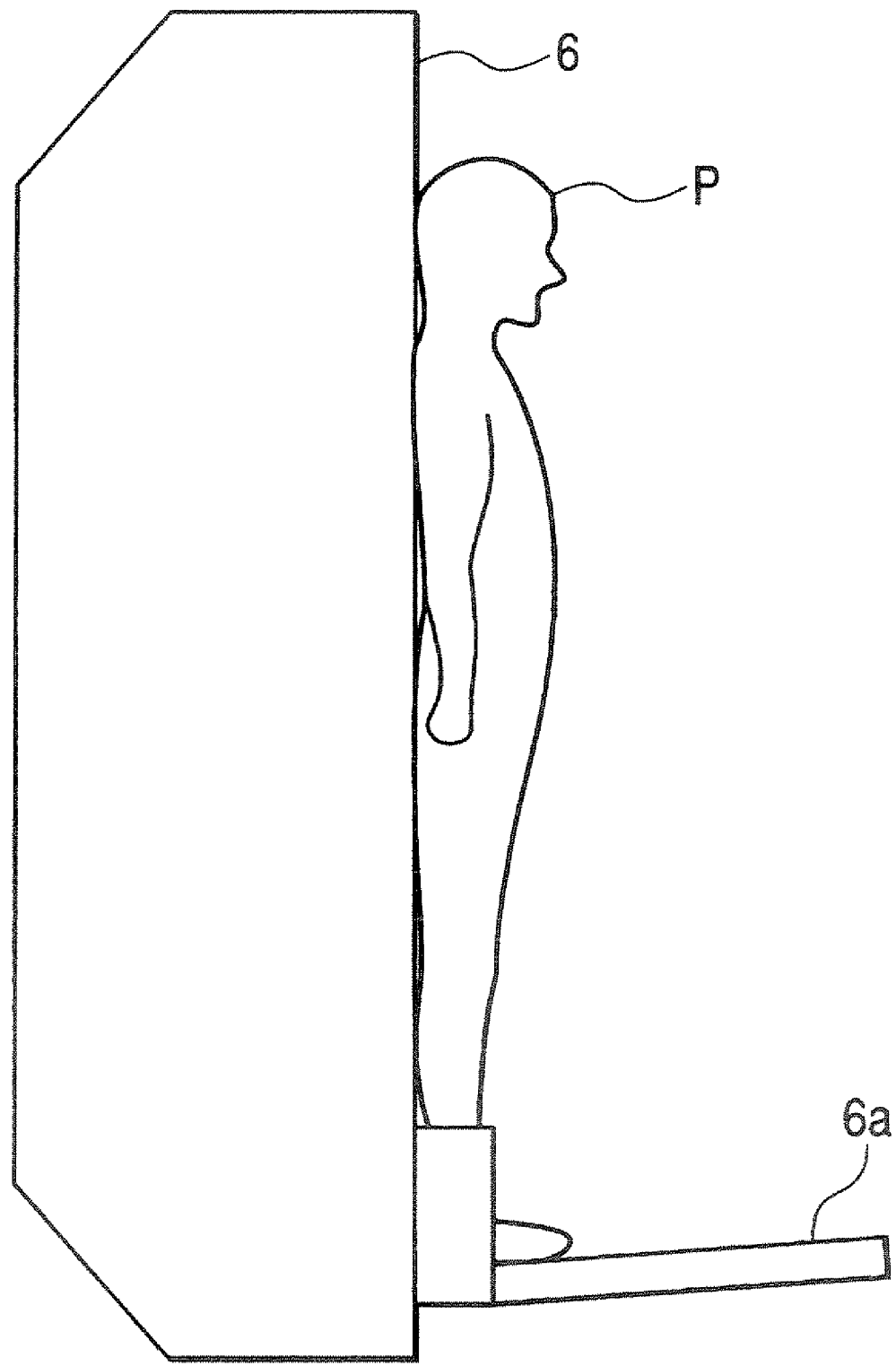
FIG. 2 is a view illustrating the configuration of the bed of FIG. 1.

FIG. 2 shows the configuration of the bed 6 of FIG. 1.

As shown in FIG. 2, a foot rest 6a is provided at one end of the bed 6. The foot rest 6a allows an object P to be diagnosed in a lifting position after the object P is placed on the bed 6. In other words, the object P can be diagnosed, lifting on the foot rest 6a. The diagnosis in lifting position is called a lifting mode and, in general, the maximum stroke of an angle of inclination of the bed 6 in the lift position is about 89 degrees.

In order to shift the usual imaging mode in which the bed 6 is in a horizontal position with an angle of inclination of 0 degree into the lifting mode, an operator inputs an order for lifting the bed 6 to the controller 5 through the operation panel 9. When a control signal is transmitted from the controller 5 to the bed lifting mechanism 7, the bed 6 is lifted by a maximum inclination angle of 89 degree by the operation of the bed lifting mechanism 7.

The maximum inclination angle of the bed 6 may be set to another value, not the maximum stroke of 89 degree by operating the operation panel 9. Therefore, a plurality of lifting modes for stopping the bed at set maximum inclination angle maybe stored in the beds top position controller 8. When a plurality of lifting modes is stored as described above, setting information for a maximum inclination angle is transmitted from the operation panel 9 to the bed stop position controller 8 through the controller 5 and then stored in the bed stop position controller 8 as a lifting mode.

For the setting operation of a maximum inclination angle, the bed stop position controller 8 is provided with a maximum inclination angle setting portion 8a, a maximum inclination angle storing portion 8b, and a maximum inclination angle selecting portion 8c. The maximum inclination angle setting portion 8a writes single or several maximum angles of inclination into the maximum inclination angle storing portion 8b according to setting information about single or several maximum angles of inclination that are transmitted through the controller 5 through the operation panel 9. Accordingly, the single or several maximum angles of inclination transmitted from the maximum inclination angle setting portion 8a and a default (initial value) of the maximum inclination angle as a candidate are stored in the maximum inclination angle storing portion 8a. Further, a maximum inclination angle stored in the maximum inclination angle storing portion 8a can be changed by transmitting changed information for the maximum inclination angle to the maximum inclination angle storing portion 8a through the controller 5 by operating the operation panel 9.

When selection information for a lifting mode and a maximum inclination angle is transmitted through the controller 5 by operating the operation panel 9, the maximum inclination angle selecting portion 8c reads out a corresponding maximum inclination angle indicated by the maximum inclination angle storing portion 8b and transmits a control signal to the bed lifting mechanism 7 to stop the bed 6 at the selected maximum inclination angle.

Further, the operation panel 9 is provided with a shift button for shifting several lifting modes by one touch.

Figure 3:
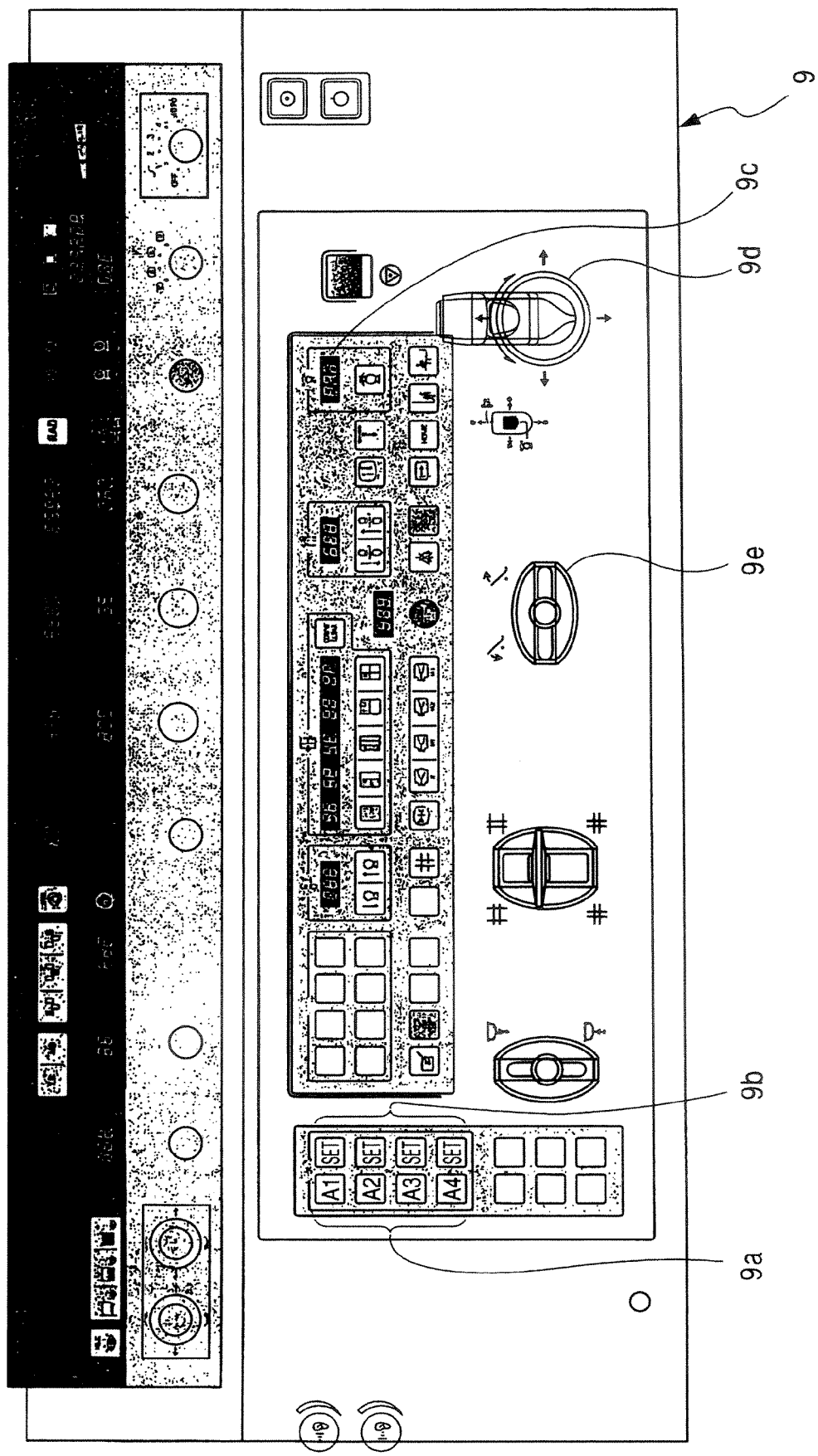
FIG. 3 is a view of an operation panel of FIG. 1.

FIG. 3 is a view showing an example of the operation panel 9 of FIG. 1.

The operation panel 9 is, including a variety of switches and levers needed for common operations in an X-ray diagnostic apparatus, provided with switches for setting, selecting, and shifting a maximum inclination angle, and selecting a lifting mode. When an operator presses any one of the left switches 9a to turn 'ON', the pressed switch is lighted on and a lifting mode in which the bed 6 stops at a desired maximum inclination angle is selectable.

A predetermined angle is set for each shift switch 9a before diagnosis. For example, when a shift switch 9a indicated by A1 is pressed, a lifting mode including a maximum inclination angle is selected and another lifting mode including another maximum inclination angle is selected, when another shift switch 9a indicated by A2 is pressed. Further, when a set button 9b at the right of each shift switch 9a is pressed, a maximum inclination angle for each shift switch can be set. When a maximum inclination angle is set, for example, a current maximum inclination angle is displayed on an angle display panel 9c. Accordingly, an operator can change a maximum inclination angle by turning an angle setting dial 9d.

After selecting a lifting mode, an operator lifts the bed 6 by moving a lifting lever 9e left or right. When the bed lifts from the horizontal position to lifting position, it can stops automatically at a maximum inclination angle selected by the shift switch 9a.

On the other hand, when the all shift switches 9a are lighted off, the lifting mode is turned 'OFF'.

When a lifting mode in which the bed stops at a desired maximum inclination angle is selected by operating the operation panel 9 before a lifting position diagnosis, for example, selected information for the lifting mode is transmitted to the bed stop position controller 8 through the controller 5. After receiving the selected information, the bed stop position controller 8 transmits a control signal to the bed lifting mechanism 7 and then the bed lifting mechanism 7 controls the position of bed 6 such that the bed 6 stops at the maximum inclination angle for the selected lifting mode. As a result from the above operation, the bed 6 can stop automatically at the desired maximum inclination angle stored as the lifting mode.

It may be possible to shift the lifting modes during diagnosis in a lift position. Further, by giving an order to stop the bed 6 through the operation panel 9 while the bed 6 moves, an operator controls the bed lifting mechanism 7 through the controller 5 and can manually stop the bed 6 simultaneously with the operation of the operation panel 9.

Figure 4:
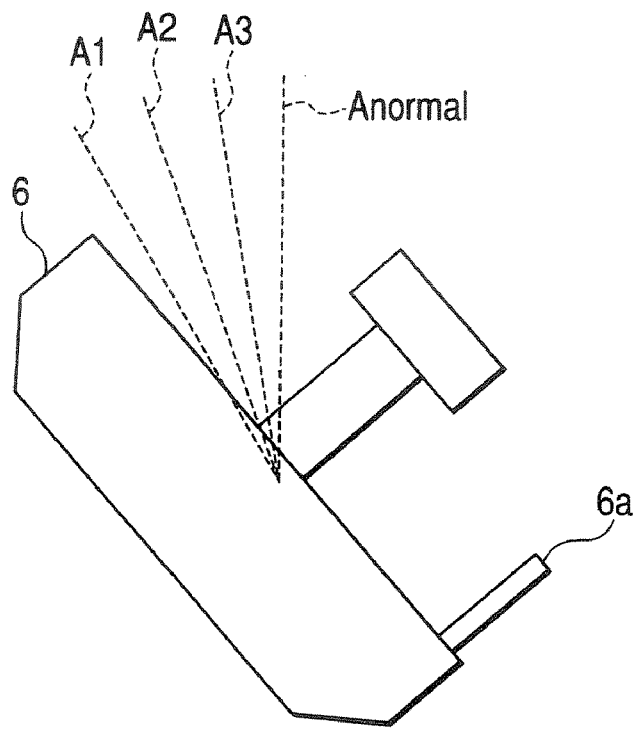
FIG. 4 is a view of an example for setting a maximum inclination angle of the bed of FIG. 2.

FIG. 4 is a view showing an example of setting of maximum angles of inclination for the bed 6 in FIG. 2.

As indicated by dotted lines in FIG. 4, maximum angles of inclination for the bed 6 are set to as A1, A2, and A3 under an A normal angle of 89 degrees and they are stored in a unit as lifting modes. According to the above configuration, when operating the bed 6, an operator can easily shift the lifting modes that operate the bed 6 to the maximum stroke of A normal of 89 degrees and to an angle of inclination of A1, A2, or A3 having a maximum inclination angle under the maximum stroke that does not discomfort an object P. Accordingly, even though the bed 6 moves, an operator can change a maximum inclination angle of the bed 6 in advance, or while the bed 6 moves or diagnosis is processed, depending on the conditions of an object P to prevent the object P from falling forward.

As described above, according to the X-ray diagnostic apparatus 1 and the bed apparatus 4, an operator of the X-ray apparatus 1 can set a maximum inclination angle of the bed 6 depending on an object P.

According to the X-ray diagnostic apparatus 1 and the bed apparatus 4, it may be possible to improve a safety for an object P by preventing an object P from falling forward, while the bed 6 moves for diagnosis in a lift position. In a lifting position diagnosis, when the angle of inclination of the bed 6 is 89 degrees, an object P intends to feel as if he/she falls forward. In this case, in conventional X-ray diagnostic apparatus 1, an operator should manually stop the bed 6 at an angle of inclination that does not discomfort an object P, thus should constantly pay attention to the operating of the bed 6.

On the other hand, according to the X-ray diagnostic apparatus 1 and the bed apparatus 4 shown in FIG. 1, a maximum inclination angle of the bed 6 can be set in advance as a lifting mode that dose not discomfort an object P. Accordingly, when an operator sets a lifting mode of a maximum inclination angle for an object P, the object P is prevented from falling forward. As a result, an operator needs not to pay attention carefully in the operating of the bed 6, and the efficiency in diagnosis can be improved.

Further, in addition to when the bed 6 is erected, when the bed 6 falls down, it is also possible to prevent an object P from falling down. Accordingly, when the bed 6 moves down, as the bed is erected, the safety and the efficiency in operation by an operator can also be improved.

Figure 5:
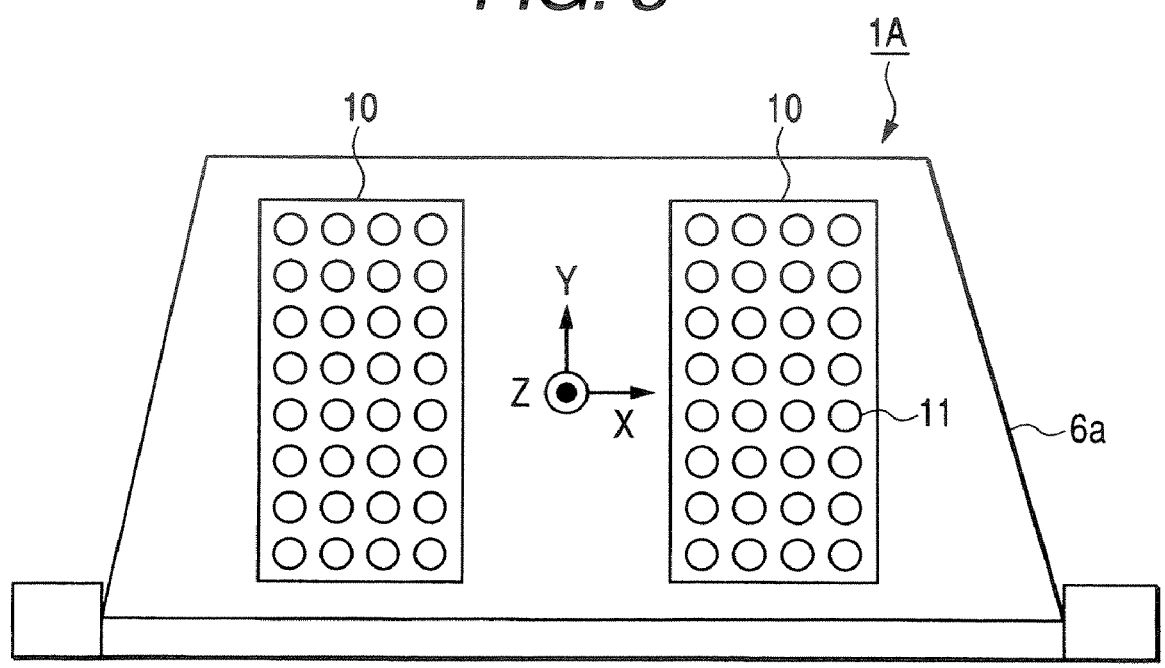
FIG. 5 is schematic view of a bed of an X-ray diagnostic apparatus according to a second embodiment of the invention.
Figure 6:
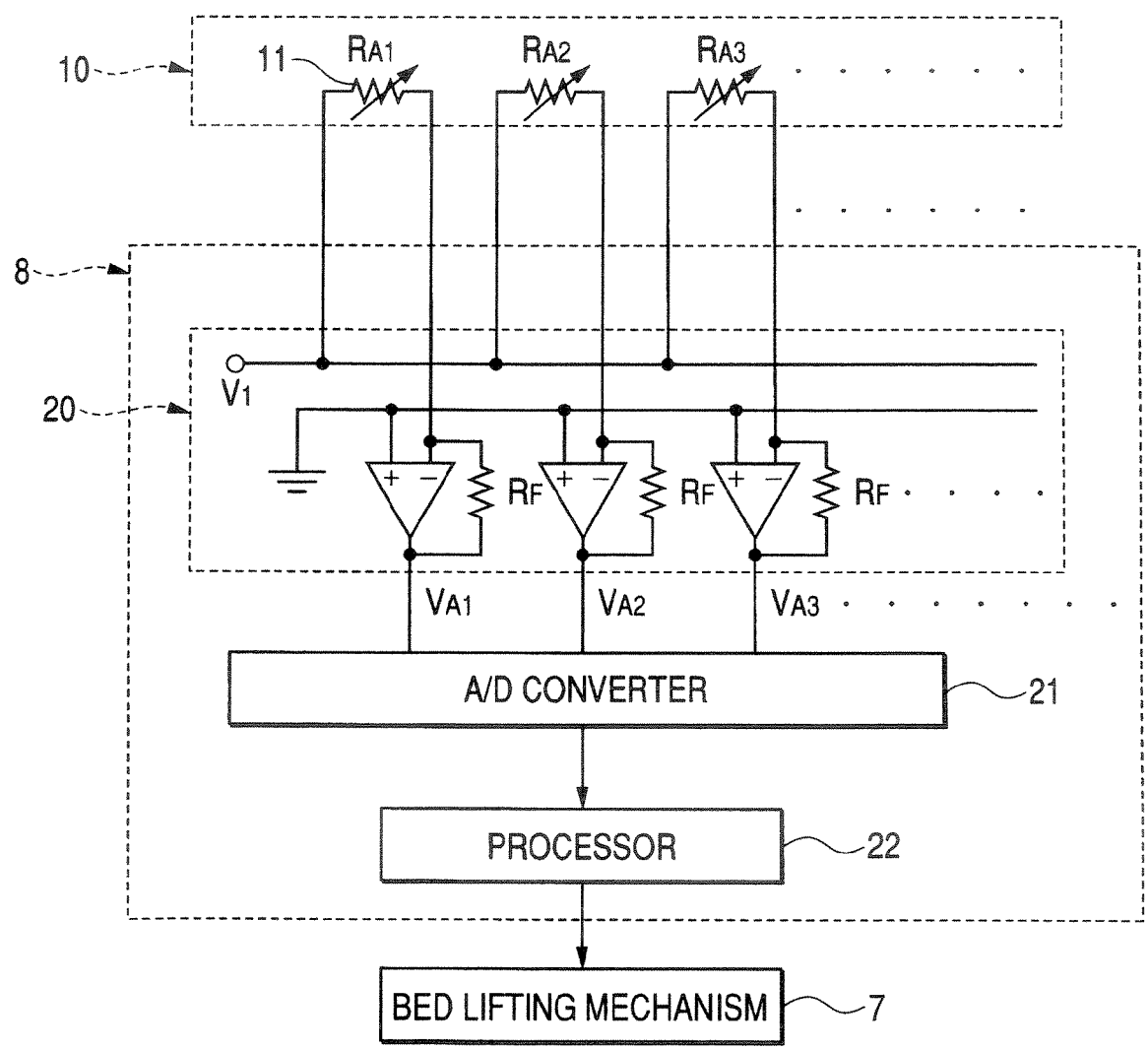
FIG. 6 is a block diagram illustrating a bed stop position controller for an X-ray diagnostic apparatus according to the second embodiment of the invention.

FIG. 5 is a view showing the configuration of a bed 6 of an X-ray diagnostic apparatus according to a second embodiment of the invention and FIG. 6 is a block diagram illustrating the function of the bed stop position controller of an X-ray diagnostic apparatus according to the second embodiment.

As shown in FIGS. 5 and 6, an X-ray diagnostic apparatus 1A is different from the X-ray diagnostic apparatus 1 shown in FIG. 1, in the configuration that a sheet-shaped pressure sensor 10 is provided with the foot rest 6a of the bed 6 and the function of the bed stop position controller 8. Because the other configurations are substantially not different from those in the X-ray diagnostic apparatus 1 shown in FIG. 1, the bed 6 and the bed stop position controller 8 are illustrated only, and the same components are represented by the same reference numerals for avoiding repetition.

In the X-ray diagnostic apparatus 1A, as shown in FIG. 5, a sheet-shaped pressure sensor 10 is provided to the foot rest 6a of the bed 6. A pressure-sensitive portion of the sheet-shaped pressure sensor 10 includes a sensor 11 that converts pressure into an electric signal. The sheet-shaped pressure sensor 10, for example, may include a plurality of sensors 11 that is two-dimensionally arranged. Two sheet-shaped pressure sensors 10 are arranged at the position where the feet of an object P is placed and can detect the pressure by the feet of the object P as an electric signal.

Further, several sensors 11 are arranged at the feet's position. The number of the sensor 11 is determined as much as at least the number required estimating the center of an object P. Each sensor 11 can be identified by the bed stop position controller 8. Accordingly, for example, a three-dimensional XYZ coordinate system may be constructed.

Figure 7:
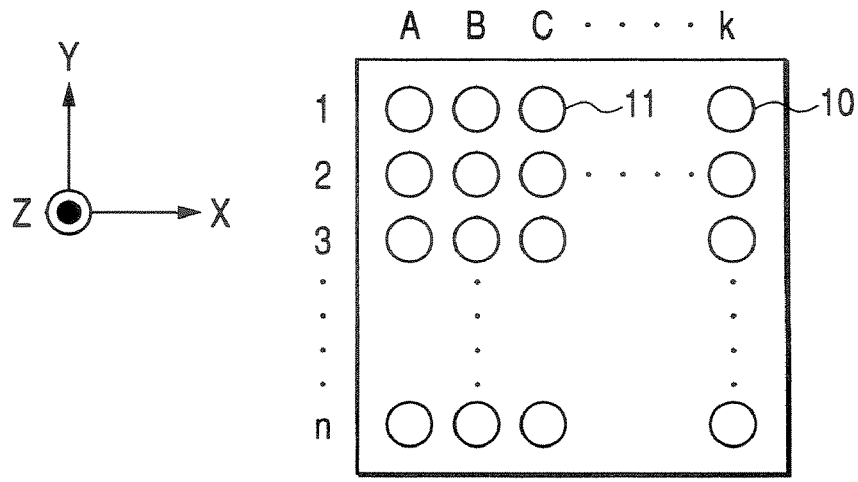
FIG. 7 is a view of an example of identification information for each sensor in a sheet-shaped pressure sensor of FIG. 5.

FIG. 7 is a view showing an example of identification information of each sensor 11 provided to the sheet-shaped pressure sensor 10 shown in FIG. 5.

As shown in FIG. 7, each sensor 11 is two-dimensionally arranged. As for the aforementioned configuration, when identification signs are given such as A, B, C, . . . , and X in one direction and 1, 2, 3, . . . , and n in the other direction, each sensor 11 can be identified by the signals given such as A1, A2, . . . An, B1, B2, . . . , Bn, . . . , k1, k2, . . . , and kn. Further, in an XYZ coordinate system, the tow-dimensional coordinates of each sensor 11 can be represented by A1 ($X_{A1}, Y_{A1}$), A2 ($X_{A2}, Y_{A2}$), . . . , An ($X_{An}, Y_{An}$), B1 ($X_{B1}, Y_{B1}$), B2 ($X_{B2}, Y_{B2}$), . . . , Bn ($X_{Bn}, Y_{Bn}$), . . . , k1 ($X_{k1}, Yk_1$), B2 ($X_{k2}, Y_{k2}$), . . . , kn ($X_{kn}, Y_{kn}$).

On the other hand, as shown in FIG. 6, the bed stop position controller 8 includes an amplifier 20, an A/D converter 21, and a processor 22. The sensors A1, A2, A3, . . . provided to the pressure-sensitive portion of the sheet-shaped pressure sensor 10 may be variable resistors $R_{A1}, R_{A2}, R_{A3}, \ldots$ , respectively, of which resistant values are changed depending on pressure. Outputs out of the sensors A1, A2, A3, . . . are respectively transmitted to the amplifier 20 and amplified into detection signals of voltages $V_{A1}, V_{A2}, V_{A3}, \ldots$ , thereafter, transmitted to the A/D converter 21. The A/D converter 21 applies A/D conversion to the detection signals of the voltages $V_{A1}, V_{A2}, V_{A3}, \ldots$ received from the amplifier 20, and the detection signals digitalized accordingly are transmitted to the processor 22.

In the processor 22, identification information and positional information (coordinates) of each sensor 11 is stored in advance, so that voltages $f_{A1}, f_{A2}, f_{A3}, \ldots$ for the sensors A1, A2, A3, . . . are obtained from the detection signals of the voltages $V_{A1}, V_{A2}, V_{A3}, \ldots$ received from the A/D converter 21. On the other hand, in the processor 22, the center coordinates ($X_G, Y_G$) of an object P is estimated through the following equation 1 using the coordinates A1 ($X_{A1}, Y_{A1}$), A2 ($X_{A2}, Y_{A2}$), A3 ($X_{A3}, Y_{A3}$) . . . and the voltages $f_{A1}, f_{A2}, f_{A3}, \ldots$ for the sensors A1, A2, A3, . . . .

$$X_G = \frac{\sum_{t=1}^{n} f_{At} \times X_{At}}{\sum_{t=1}^{n} f_{At}} \qquad \text{Equation 1}$$

$$Y_G = \frac{\sum_{t=1}^{n} f_{At} \times Y_{At}}{\sum_{t=1}^{n} f_{At}}$$

In the processor 22, a tolerance for a center position of an object P is set in advance. In the processor 22, it is determined whether the center coordinates ($X_G, Y_G$) of an object P calculated from the above equation 1 are included within the preset tolerance. When it is determined that the calculated center coordinates ($X_G, Y_G$) of an object P is out of the tolerance, an order for stopping the bed 6 is outputted to the bed lifting mechanism 7. According to the aforementioned operation, the bed 6 automatically stops.

A modal on/off shift is possible in the estimating function of a center position of an object P in the bed stop position controller 8. In other words, while the estimating function of a center position of an object P is turned on, a center detection mode, which stops the lifting operation of the bed 6 according to the estimated center position of an object P, can be set.

A selection order of the center detection mode may be sent to the bed stop position controller 8 through the controller 5 from the operation panel 9. In this process, a center detection mode may be selected by one touch through a selection button on the operation panel 9. The center detection mode is selectable not only during stop of the bed 6, but diagnosis or movement of the bed 6.

The tolerance for the center position of an object P may also be changed at any timing including the lifting operation of the bed 6 by sending an order for changing the tolerance to the bed stop position controller 8 through the controller 5 from the operation panel 9. In particular, when a plurality of tolerances is set in advance, a desired tolerance can be easily selected using the selection button even though diagnosis is being processed.

The stopping order of the bed 6 in the center detection mode of the X-ray diagnostic apparatus 1A is described hereafter.

Figure 8:
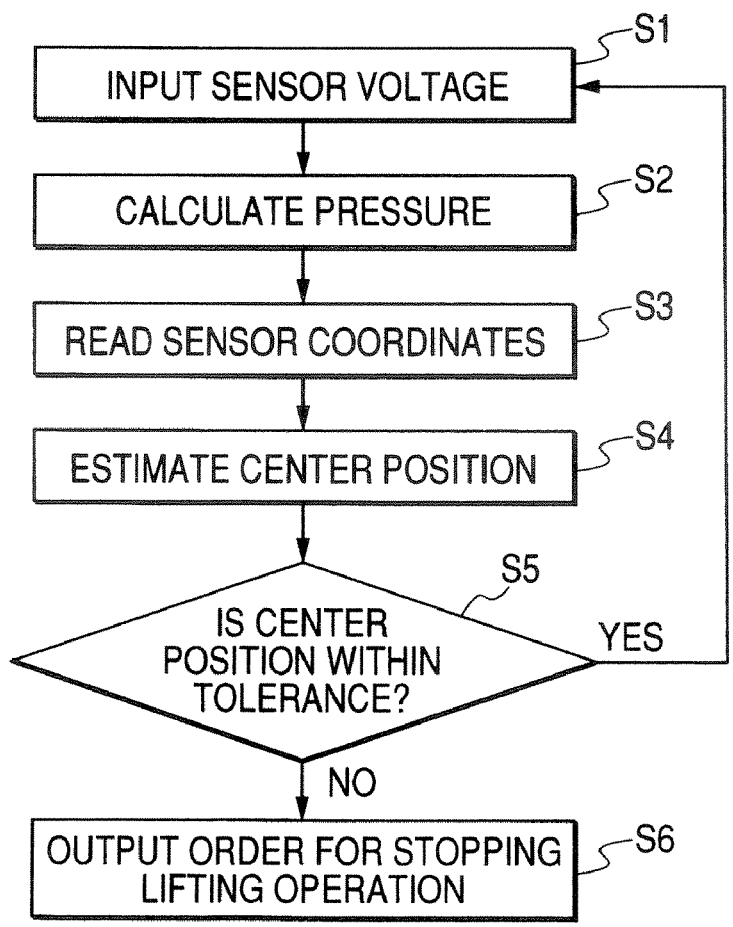
FIG. 8 is a flowchart illustrating a processing order of a processor in a center detection mode of the X-ray diagnostic apparatus of FIG. 5.

FIG. 8 shows a flowchart illustrating a processing order in the processor 22 in the center detection mode of the X-ray diagnostic apparatus 1A shown in FIG. 5. Reference symbol S represents each step in the flowchart.

At Step S1, when the bed 6 where an object P is placed lifts, the feet of the object P press each sensor 11 in the sheet-shaped pressure sensor 10 provided to the foot rest 6a of the bed 6. During this process, a resistant value of each sensor 11 changes and the processor 22 inputs a voltage for each sensor outputted according to the pressure transmitted through the amplifier 20 and the A/D converter 21 from each sensor 11.

At Step S2, the processor 22 calculates pressure applied to each sensor 11 from each inputted sensor voltage. A resistant characteristic against the pressure for each sensor 11 is referred to calculate the pressure.

At Step S3, the processor 22 refers positional information for each sensor 11 stored in advance and reads out coordinates for each sensor 11.

At Step S4, the processor 22 estimates the center position of the object P through the equation 1 using the read coordinates for each sensor 11 and the pressure applied to each sensor 11.

At Step 5, the processor 22 determines whether the estimated center position of the object P is included within a preset tolerance. When the estimated center position of the object P is within the preset tolerance, the processor 22 returns to Step S1 and re-inputs sensor voltages for each sensor 11.

On the other hand, when the estimated center position of the object P is out of the preset tolerance, the processor 22 allows a stop order of the bed 6 to output to the bed lifting mechanism 7 at Step 5. As a result, when it is detected that the center position of the object P is out of the preset tolerance by the processor 22, the bed automatically stops.

Figure 9:
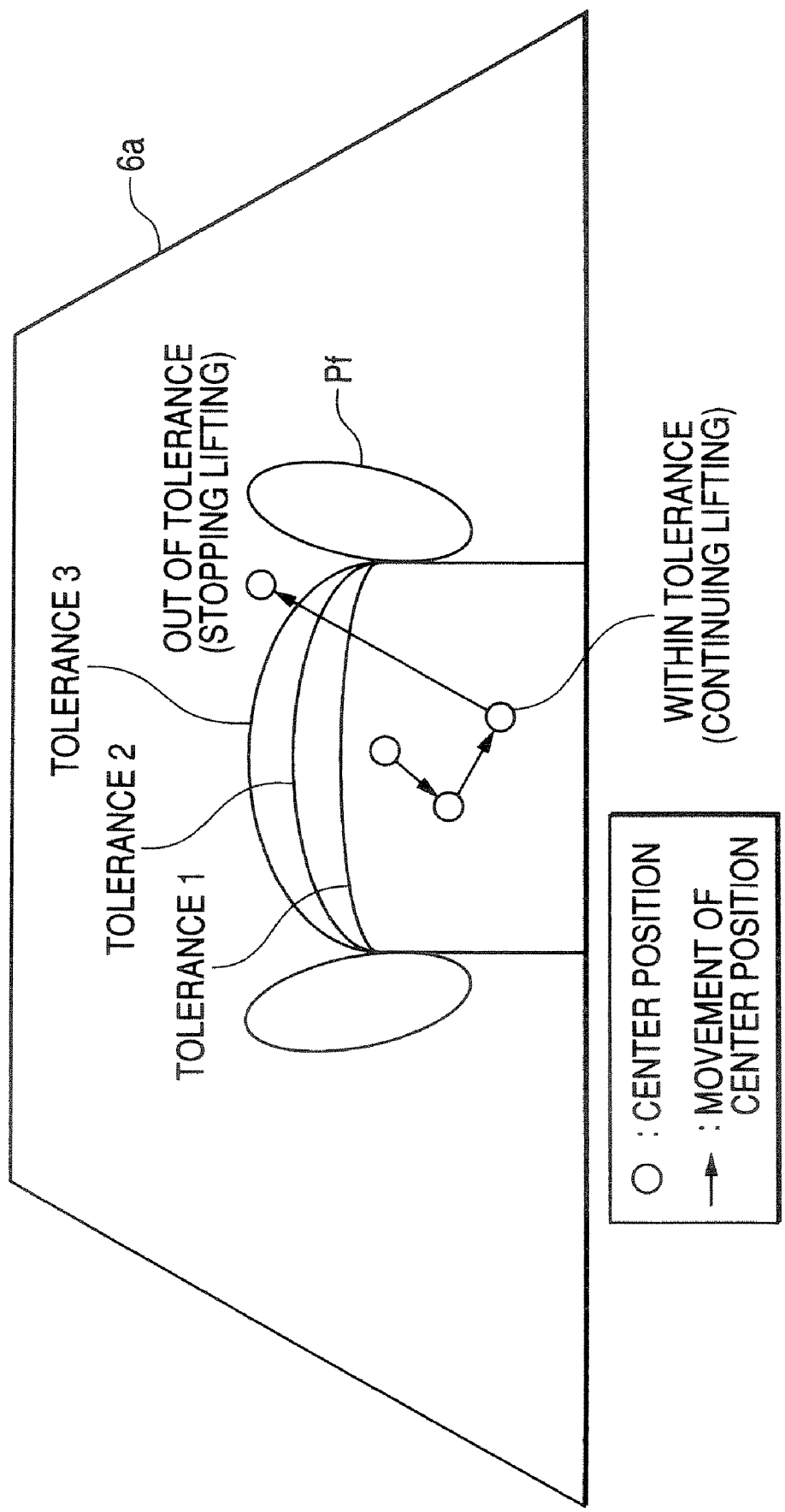
FIG. 9 is a view of paths of center position and setting a tolerance for the center position in the center detection mode of the X-ray diagnostic apparatus of FIG. 5.

FIG. 9 is a view showing an example setting a tolerance for an estimated center position and paths of the center position in the center detection mode of the X-ray diagnostic apparatus 1A shown in FIG. 5.

Feet Pf of an object P are placed on the foot rest 6a in FIG. 9. As indicated by a solid line in FIG. 9, when several tolerances for a center position of an object P are set in advance, an operator can easily select a tolerance during diagnosis. As a center position of an object P moves as shown by arrows and circles, while the center position is within the tolerance, the bed 6 continuously lifts. However, when the center position gets out of the tolerance, the processor 22 outputs an order for stopping the lifting operation of the bed 6 and the bed 6 automatically stops.

According to the X-ray diagnostic apparatus 1A, a center position of an object P is estimated by detecting pressure by feet, and when it is determined the estimated center position of the object P is out of a preset tolerance, the bed 6 automatically stops the lifting operation.

Accordingly, according to the X-ray diagnostic apparatus 1A, while the condition of an object P is constantly watched, when the object P seems to fall forward, the bed 6 can automatically stop the lifting operation. According to the above configuration, an operator does not need to constantly watch the condition of an object P in the operating of a bed. As a result, an operator does not need to carefully pay attention to the lifting operation and diagnostic efficiency is improved, and an object P can be prevented from falling forward and secured.

A method setting a tolerance for a center position can be arbitrarily selected. For example, a threshold value for the amount of shift of a center position may be set to as a tolerance. Further, in the X-ray diagnosis apparatus 1A shown in FIG. 5, although a center position is detected as moving information indicating a moving distance of an object P on the basis of pressure by feet, the X-ray diagnostic apparatus 1A may be configured such that it can obtain moving information other than the center position. For example, the X-ray diagnostic apparatus 1A may be configured such that it obtains a moving distance of an object P using an infra-red sensor 11. Accordingly, when any moving information satisfies a predetermined condition, the bed lifting mechanism 7 may be controlled such that the bed 6 automatically stops.

The X-ray diagnostic apparatuses 1 and 1A or the bed apparatus 4 in the embodiments may be combined with one another. A condition required for stopping the bed 6 is not only a maximum inclination angle of the bed 6 or a center position of an object P, but arbitrarily set. Further, a function that is the same as those of the bed apparatus 4 may be applied to a bed apparatus used in association with medical apparatuses or medical instruments other than the X-ray diagnostic apparatuses 1 and 1A.

What is claimed is:

1. An X-ray diagnostic apparatus, comprising:
   a diagnostic information obtaining unit configured to obtain diagnostic information of an object by irradiating X-rays;
   a bed where the object placed;
   a bed lifting unit configured to lift the bed; and
   a bed stop position control unit configured to determine a stop condition and to control the bed lifting unit such that the bed stops at a position under a maximum stroke according to the predetermined stop condition, wherein the bed stop position control unit sets a maximum inclination angle of the bed as the stop condition and controls the bed lifting unit such that the bed stops at the maximum inclination angle,
   wherein the bed stop position control unit includes
      a maximum inclination angle storing portion configured to store a plurality of positions of the bed each of which can be set as a maximum inclination angle of the bed; and
      a maximum inclination angle selecting portion configured to select a position of the bed indicated as the stop condition from the maximum inclination angle storing portion.

2. The X-ray diagnostic apparatus according to claim 1, further comprising:
   a moving information obtaining unit configured to obtain moving information indicating a moving distance of an object,
   wherein, when the moving information obtained by the moving information obtaining unit satisfies a predetermined condition, the bed stop position control unit controls the bed lifting unit such that the bed stops.

3. The X-ray diagnostic apparatus according to claim 2,
wherein the moving information obtaining unit estimates a center position of an object as the moving information, and the bed stop position control unit controls the bed lifting unit such that the bed stops, when it is determined that the center position is out of a tolerance.

4. The X-ray diagnostic apparatus according to claim 3,
wherein the bed stop position control unit obtains an order to change the tolerance for the center position from an input device at any time of the lifting operation of the bed and changes the tolerance.

5. The X-ray diagnostic apparatus according to claim 1,
wherein the bed stop position control unit includes
a maximum inclination angle setting portion configured to store a candidate for the maximum inclination angle to the maximum inclination angle storing portion and then change a candidate for a maximum inclination angle stored in the maximum inclination angle storing portion according to information out of an operation unit.

6. The X-ray diagnostic apparatus according to claim 1,
wherein the bed stop position control unit includes
a switch configured to indicate the maximum inclination angle of the bed as the stop condition to the maximum inclination angle selecting portion.

7. The X-ray diagnostic apparatus of claim 1, further comprising:
an X-ray irradiating unit; and
an X-ray detector unit.

8. A method for controlling a bed of an X-ray diagnostic apparatus, the method comprising:
lifting a bed;
determining a stop condition; and
stopping the bed at a position under a maximum stroke according to the predetermined stop condition,
wherein the determining step includes determining a maximum inclination angle of the bed as the stop condition, and the stopping step includes stopping the bed at the maximum inclination angle,
the method further comprising
storing a plurality of positions of the bed, each of which can be set as a maximum inclination angle of the bed, and selecting a position of the bed indicated as the stop condition from the stored positions.

9. The method for controlling a bed of an X-ray diagnostic apparatus according to claim 8, further comprising:
obtaining moving information indicating a moving distance of an object,
wherein the bed stops, when the obtained moving information satisfies a predetermined condition.

10. The method for controlling a bed of an X-ray diagnostic apparatus according to claim 9,
wherein a center position of an object is estimated as the moving information, and the bed stops, when it is determined that the center position is out of a tolerance.

11. The method for controlling a bed of an X-ray diagnostic apparatus according to claim 10,
wherein, when an order to change the tolerance for the center position from an input device at any time of the lifting operation of the bed is received, the tolerance changes.

12. The method for controlling a bed of an X-ray diagnostic apparatus according to claim 8,
wherein a candidate for the maximum inclination angle is stored and the stored candidate for the maximum inclination angle is changed according to information out of an operation unit.

13. The method for controlling a bed of an X-ray diagnostic apparatus according to claim 8,
wherein the position of the bed determined as the stop condition is selected from the stored positions of the bed by a switch.

\* \* \* \* \*